United States Patent [19]

Johnson

[11] Patent Number: 4,706,061
[45] Date of Patent: Nov. 10, 1987

[54] COMPOSITION SENSOR WITH MINIMAL NON-LINEAR THERMAL GRADIENTS

[75] Inventor: Robert G. Johnson, Minnetonka, Minn.

[73] Assignee: Honeywell Inc., Minneapolis, Minn.

[21] Appl. No.: 901,215

[22] Filed: Aug. 28, 1986

[51] Int. Cl.$^4$ .................. H01L 7/00; H01L 29/06; B32B 3/10; B32B 15/04

[52] U.S. Cl. ........................... 338/34; 156/647; 338/292; 338/293; 338/319; 357/55; 428/136; 428/137; 428/210; 428/620; 428/621; 428/615; 428/627; 428/698

[58] Field of Search ................ 428/698, 699, 614–617, 428/620, 621, 627, 136, 137, 209, 210; 73/25, 26, 27 R, 204, 719–721, 725–727; 156/647; 338/25, 292, 293, 319, 34, 318, 2–5; 357/55; 422/98

[56] References Cited

U.S. PATENT DOCUMENTS

| | | | |
|---|---|---|---|
| 3,986,200 | 10/1976 | Allison | 156/647 |
| 4,214,478 | 7/1980 | Lauterbach | 73/204 |
| 4,304,130 | 12/1981 | Peter et al. | 73/204 |
| 4,412,449 | 11/1983 | Eiermann et al. | 73/204 |
| 4,472,239 | 9/1984 | Johnson et al. | 156/647 |
| 4,501,144 | 2/1985 | Higashi et al. | 73/204 |
| 4,511,878 | 4/1985 | Shimada et al. | 73/720 |
| 4,548,078 | 10/1985 | Bohrer et al. | 357/55 |
| 4,581,928 | 4/1986 | Johnson | 338/25 |
| 4,600,934 | 7/1986 | Aine et al. | 156/647 |

OTHER PUBLICATIONS

Fabrication of Novel 3-D Microstructures by Anisotropic Etching of (100) & (110) Silicon, IEEE Transactions on Electron Devices, vol. ED-25, No. 10 (10/78), Ernest Bassous.

Primary Examiner—Ellis P. Robinson
Assistant Examiner—James B. Monroe
Attorney, Agent, or Firm—Omund R. Dahle

[57] ABSTRACT

A gaseous composition sensor which is a microstructure device comprising a heated planar thin film diaphragm sensor member suspended over a shallow flat bottomed etched pit in a single crystal silicon substrate.

9 Claims, 7 Drawing Figures

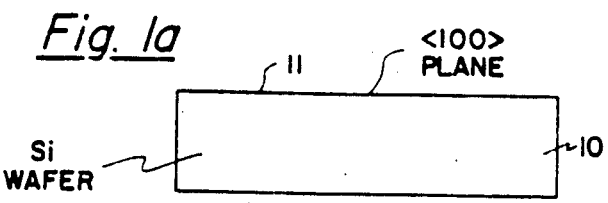
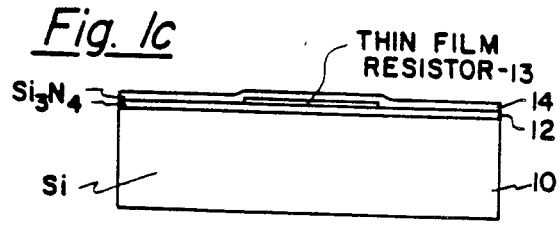
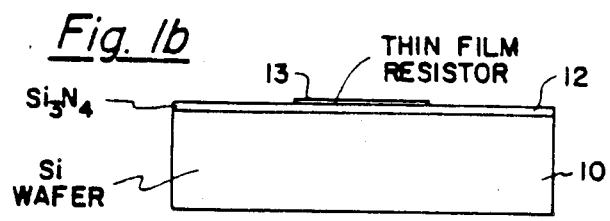
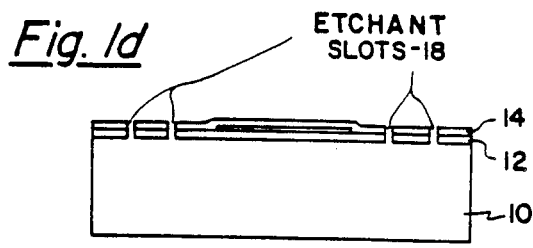
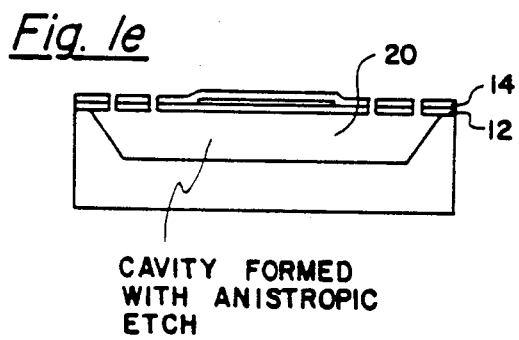

COMPOSITION SENSOR WITH MINIMAL NON-LINEAR THERMAL GRADIENTS

BACKGROUND AND SUMMARY OF THE INVENTION

The field of the invention is microbridge gas composition sensors.

In a microbridge used to measure gaseous composition changes, non-linear thermal gradient edge effects occur which cause response to pressure changes. This can cause false indications of composition changes.

In the present invention, the edge effects are greatly reduced or eliminated, and the composition signal is enhanced by making the spacing between the heated element and the cold sink much smaller than in prior art structures.

BRIEF DESCRIPTION OF THE DRAWINGS

FIGS. 1a-1e show progressive stages in the fabrication of the invention.

FIG. 3 shows an individual etch pit in the underlying silicon resulting from an individual slot through the nitride diaphragm.

DESCRIPTION

Figure 2:
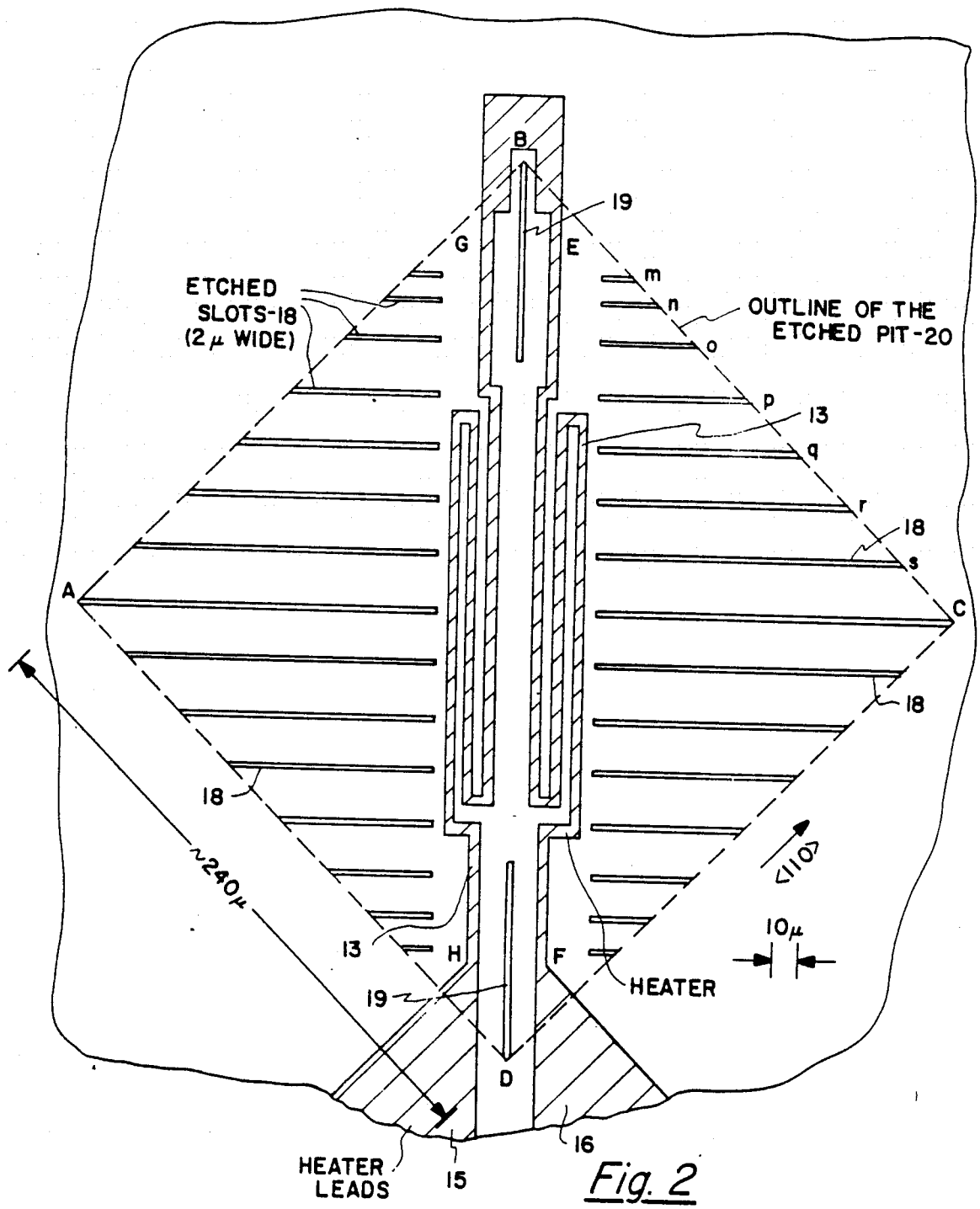
FIG. 2 is a layout of a preferred embodiment of the composition sensor design.

This invention teaches a gas composition sensor which is based on the dissipation of thermal energy. Generally, the device is a microstructure comprising a heated planar thin-film sensor member on a silicon wafer. The thin-film sensor member is isolated primarily by the gaseous medium from a parallel silicon heat-sink surface. Referring now to FIGS. 1a-1e a sequence of fabrication steps is shown. First there is provided a semiconductor body comprising (100) silicon having a (100) plane and a <110> direction. This single crystal silicon wafer or substrate 10 with (100) crystal lattice orientation at the planar surface 11 is cleaned and polished (FIG. 1a). Silicon is chosen because of its adaptability to precision etching techniques and ease of electronic chip producibility. Next, a silicon nitride ($Si_3N_4$) diaphragm layer 112 (a dielectric) is deposited on the silicon surface. A thin-film resistor 13 for the heater is deposited on the $Si_3N_4$ layer (FIG. 1b) and patterned after the configuration shown in FIG. 2. Permalloy is preferred for the heater 13 because permalloy can be precisely deposited by sputtering a layer of the desired thickness such as approximately 800 Å. The resistor 13 may be about 5 microns in width as shown in FIG. 2. Pads 15 and 16 provide contacts for applying electrical power to the heater. Another layer of $Si_3N_4$ 14 is deposited over the existing $Si_3N_4$ 12 and the thin-film resistor 13 (FIG. 1 c). Each of the layers 12 and 14 may be on the order of 5000 Å in thickness so that the diaphragm is about a micron thick.

By means of conventional masking and etching techniques, a plurality of closely spaced slots 18 for etchant outlets are cut into and through the silicon nitride layers 12 and 14 (FIG. 1d). The slots 18 are approximately parallel to each other, and approximately parallel to the lines of lateral heat flow from the heater over most of the diaphragm area, and are oriented substantially at an angle of 45° to the <110> direction although slight departures from 45° are permissible to orient the slots more nearly parallel to the lines of heat flow outward from the heater. The slots 18 are cut in the pattern as denoted in FIG. 2. The multiple slots 18 by themselves would not complete the etching beneath the entire diaphragm in the most rapid manner. Thus it is desirable to add the two slots 19 which are at right angles to the slots 18 and which lie along a diaphragm center-line drawn from B to D. These two additional slots 19 are also at an angle of substantially 45° to the <110> direction. The upper slot 19 has an upper end thereof terminating at B and the lower slot 19 has a lower end thereof terminating at D. The substrate is immersed in an anisotropic silicon etchant such as KOH plus isopropyl alcohol. This is an anisotropic etchant that does not appreciably attack the silicon nitride. A thermal isolation, flat-bottomed pit or cavity 20 is formed in the silicon underlying the $Si_3N_4$ diaphragm.

If a single one of the slots 18' is considered, FIG. 3 discloses the cavity pattern resulting from that one distinct slot in the diaphragm. It will be noted that, for the slot 18' alone, the (111) planes would act as a natural etch stop along the edges.

Close spacing of the etch slots 18 (i.e. about 20 microns spacing) provides overlapping of the individual cavities and will result in the shallow cavity of the pattern shown in FIG. 2. Thus the desired front-surface etching of the shallow cavity 20 is accomplished by means of slots cut in the planar nitride thin film sensor member in such a way that etch pits overlap and combine to permit the formation of a flat bottomed (100) plane beneath the planar nitride film early in the etch to achieve a desired film-to-pit bottom spacing of 0.001-0.002 inches. As shown in FIG. 2 the dimensions of the pit 20 may be about 240 microns on a side. Boron doping is an alternate method to achieve an etch stop in the silicon. The closely spaced parallel etch slots 18 are of graduated lengths to define the perimeter BC, CD, BA and AD of the etched pit 20. Thus along perimeter leg BC, the outer and m,n,o,p,q,r and s of the respective parallel slots extends to the perimeter line BC. The inner ends of the parallel slots may terminate at a line extending perpendicular to the slots. This describes one quadrant of the parallel slots. The other three quadrants are laid out similarly along the perimeter legs CD, BA and AD of the shallow pit 20.

A main design objective is to make virtually all the thermal gaseous conduction from the heated film area to the underlying silicon, occur in regions of substantially linear thermal gradient. That is, the sharp non-linear gradients at the nitride edges of microbridge sensors previously evaluated are absent in this invention. Consequently the gaseous pressure effects attributable to non-linear edge gradients are also absent in this invention, and the variation of thermal conductance with composition will be practically independent of pressure.

In FIG. 2 the etch slots 18 are oriented at 45 degrees to the <110> directions. The slots, all of which are preferably 2 microns in width, are arranged to have overlapping of individual etch pits. The close spacing of slots 18 now permits the achievement of a flat bottom for the ABCD pit in a very short space of time so that the pit depth can be easily controlled in the 0.001" depth neighborhood. This is essential because the etching between the ends of the slots, for example: between E and F, causes pits to form which quickly merge to form a (100) type surface perpendicular to the primary (100) surface of the chip, and which then rapidly etches laterally toward the left, quickly meeting the similar surface etching laterally toward the right from the slot end GH. Thus the flat bottom forms quickly in a few minutes of anisotropic etching before the ABCD pit becomes very deep. The shallow pit has the following advantages: (1) it provides a larger response to composition changes, (2) it provides more conduction through the pit air space near the heater and less through the nitride film to the edge of the pit, and (3) it provides less conduction through air away from the chip to housing surfaces. Also the slots are for the most part oriented closely parallel to the thermal flow that occurs away from the heater through the nitride film. This minimizes possible temperature differences across the slots which could contribute to a pressure dependent output signal. Ideally the slots could be made to follow the flow lines exactly.

The gas composition sensor is intended to be operated at a constant temperature above ambient temperature, for example, about 135° C. above ambient. Depending on the composition of the gaseous fluid being sensed, the electrical power required to maintain the sensor at the constant temperature above ambient will change as the composition changes. For example, if moisture content of the air is being monitored, an increase in the moisture content will result in a change of power to the heater 13 being required to maintain the sensor at the constant temperature above ambient.

The embodiments of the invention in which an exclusive property or right is claimed are defined as follows:

1. A gaseous composition sensor comprising:
   a semiconductor body comprising (100) silicon and having a (100) plane and a <100> direction, a first surface of the body being substantially parallel to the (100) plane;
   a thin film layer of $Si_3N_4$ covering at least a portion of said first surface;
   square shaped diaphragm means comprising the thin film $Si_3N_4$, said square shaped diaphragm means having successive corners A,B,C and D, where corners B and D are diagonally opposite, said diaphragm means being oriented so that a line joining diaphragm means opposite corners B and D is at an angle of substantially 45° to the <110> direction, said diaphragm means further comprising resistive heater means embedded in the $Si_3N_4$ layer generally centered along the diagonal diaphragm area from corners B to D, said diaphragm means having lines of lateral heat flow from the heater means over most of the diaphragm means, said diaphragm means having perimeter lines AB, BC, CD and DA;
   a series of closely spaced approximately parallel first slots through said diaphragm, the length of said slots being aligned approximately perpendicular to the line joining corners B and D and approximately parallel to the lines of lateral heat flow from the heater over the diaphragm so that said slots are thus at an angle of substantially 45° to the <110> direction, said slots extending at the outer end to one of perimeter lines AB, BC, CD and DA, said slots providing openings through the $Si_3N_4$ to the silicon for purposes of etching the silicon;
   two additional slots called a second and a third slot aligned with each other along the line joining B and D and oriented orthogonally to said first slots, said second slot having its outer terminus at said corner B, said third slot having its outer terminus at said corner D;
   and a square shaped shallow flat bottomed anisotropically etched pit in said silicon beneath said square shaped diaphragm means and conforming to said diaphragm means in orientation and size.

2. The invention according to claim 1 in which said $Si_3N_4$ layer is about 1 micron thick.

3. The invention according to claim 1 in which said series of parallel slots are each about 2 microns in width.

4. The invention according to claim 1 in which said square shaped diaphragm means and said square shaped pit are about 240 microns on a side.

5. The invention according to claim 4 in which said shallow pit is about 0.001 inch in depth.

6. The invention according to claim 4 in which said series of parallel slots are spaced about 20 microns apart.

7. The invention according to claim 1 in which the resistive heater means is a nickel-iron alloy.

8. A method of fabricating a microbridge gaseous composition sensor comprising a silicon nitride thin film diaphragm covering a shallow depression etched into a silicon substrate, the steps comprising:
   providing a single crystal silicon substrate comprising (100) silicon and having a (100) plane and a <110> direction, with a first surface of the substrate being substantially parallel to the (100) plane;
   depositing a thin-film layer of silicon nitride onto the first surface to become a diaphragm;
   providing an electrical heater on a portion of said silicon nitride layer by forming a thin film strip of resistive metal thereon;
   planning a square depression in said silicon surface beneath said $Si_3N_4$ layer, where one side of said square is parallel with the <110> direction of said silicon, said square having first and second adjacent sides and third and fourth adjacent sides;
   preparing a first series of closely spaced parallel slots through the $Si_3N_4$ and oriented at substantially 45° to the <110> direction and to the first and second adjacent sides;
   preparing a second series of closely spaced parallel slots through the $Si_3N_4$, the slots lying in a direction parallel to the first series slots and oriented at substantially 45° to the <110> direction and to the third and fourth adjacent sides;
   said slots being of differing lengths and each slot having an exterior end terminating at the first, second, third or fourth side;
   preparing another pair of slots axially aligned with each other and oriented orthogonally to the previous defined slots and located between the first and second series of slots; and,
   applying an anisotropic etch through said slots to the silicon first surface, the slots being oriented at substantially 45° to the <110> direction, to undercut the diaphragm and create a shallow square depression.

9. A gaseous composition sensor comprising:
   a semiconductor substrate comprising (100) silicon having a (100) plane and a <110> direction;
   a thin-film layer means of $Si_3N_4$ on the semiconductor substrate surface;
   a resistive metallic heater embedded in the $Si_3N_4$ layer;
   a first series of closely spaced parallel slot means extending through the $Si_3N_4$ surrounding the location of said resistive heater, said slots being oriented at an angle of substantially 45° to the <110> direction for the purpose of providing etchant access for anisotropically etching a shallow pit in the silicon under a portion of the $Si_3N_4$;

a square shaped outline for the shallow pit, the outline having successive corners A, B, C and D, corners B and D being at diagonally opposite corners, a line connecting corners B and D being at an angle of substantially 45° to the <110> direction, the square shaped outline having perimeter sides AB, BC, CD and DA, said slot means extending at the outer end to one of the perimeter sides;

and further slot means orthogonal to said first slot means located on said BD line and having the slot means terminate at B and D.

* * * * *

UNITED STATES PATENT AND TRADEMARK OFFICE
CERTIFICATE OF CORRECTION

PATENT NO. : 4,706,061

DATED      : November 10, 1987

INVENTOR(S) : Robert G. Johnson

It is certified that error appears in the above-identified patent and that said Letters Patent is hereby corrected as shown below:

Column 3, line 31, delete <100> and substitute --<110>--.

Column 3, line 41, delete "diaphragm means" and substitute --diagonally--.

Signed and Sealed this

Twenty-fourth Day of May, 1988

Attest:

DONALD J. QUIGG

Attesting Officer

Commissioner of Patents and Trademarks